US 11,490,968 B2

(12) United States Patent
Kelley (10) Patent No.: US 11,490,968 B2
(45) Date of Patent: Nov. 8, 2022

(54) DEVICES, SYSTEMS, AND METHODS FOR LABELING OBJECTS OF INTEREST DURING A MEDICAL PROCEDURE

(71) Applicant: KARL STORZ SE & Co. KG, Tuttlingen (DE)

(72) Inventor: Kalon Kelley, Santa Ynez, CA (US)

(73) Assignee: KARL STORZ SE & Co. KG, Tuttlingen (DE)

(*) Notice: Subject to any disclaimer, the term of this patent is extended or adjusted under 35 U.S.C. 154(b) by 265 days.

(21) Appl. No.: 16/942,173

(22) Filed: Jul. 29, 2020

(65) Prior Publication Data
US 2022/0031405 A1 Feb. 3, 2022

(51) Int. Cl.
| G06K 9/00 | (2022.01) |
| A61B 34/00 | (2016.01) |
| A61B 90/00 | (2016.01) |
| G06T 7/11 | (2017.01) |
| G06F 3/01 | (2006.01) |
| G06N 3/08 | (2006.01) |

(52) U.S. Cl.
CPC ............. *A61B 34/25* (2016.02); *A61B 34/76* (2016.02); *A61B 90/37* (2016.02); *G06F 3/013* (2013.01); *G06N 3/08* (2013.01); *G06T 7/11* (2017.01); *G06T 2207/30204* (2013.01)

(58) Field of Classification Search
CPC ...................................................... G06F 3/013
See application file for complete search history.

(56) References Cited

U.S. PATENT DOCUMENTS

| 8,379,981 | B1* | 2/2013 | Prokhorov | ............. | G06V 20/49 |
| | | | | | 382/173 |
| 9,213,405 | B2 | 12/2015 | Perez et al. | | |
| 2006/0112334 | A1 | 5/2006 | Endrikhovski et al. | | |
| 2007/0076958 | A1* | 4/2007 | Venkatesh | .............. | G06V 40/19 |
| | | | | | 382/218 |
| 2014/0002352 | A1 | 1/2014 | Jacob et al. | | |
| 2016/0171299 | A1 | 6/2016 | Lee et al. | | |
| 2018/0253145 | A1* | 9/2018 | Swaminathan | ......... | G06F 3/013 |
| 2018/0268552 | A1 | 9/2018 | Wood et al. | | |
| 2019/0365252 | A1 | 12/2019 | Fernald et al. | | |

FOREIGN PATENT DOCUMENTS

EP 3210163 A1 8/2017

OTHER PUBLICATIONS

European Search Report for European Application No. 21184866.8, dated Dec. 17, 2021.

* cited by examiner

*Primary Examiner* — Hadi Akhavannik
(74) *Attorney, Agent, or Firm* — Jason H. Vick; Sheridan Ross, PC (57) ABSTRACT

A device includes a memory including instructions, and a processor that executes the instructions to determine, based on eye tracking data, that a clinician gazes at a sub-section of a display for more than a threshold amount of time during a first time period of a medical procedure, where the display displays video of the medical procedure according to a video signal. The processor executes the instructions to identify a block of the video signal that corresponds the first time period, segment a selected frame in the block of the video signal into a plurality of sub-regions, perform further processing on the plurality of sub-regions, and automatically identify an object of interest within the selected frame based on the further processing.

20 Claims, 7 Drawing Sheets

DEVICES, SYSTEMS, AND METHODS FOR LABELING OBJECTS OF INTEREST DURING A MEDICAL PROCEDURE

FIELD

The present disclosure is generally directed to devices, systems, and methods for labeling objects of interest during a procedure.

BACKGROUND

Modern medical procedures may be camera-assisted, with video and/or still images of the procedure being recorded and stored in a database. Post-operation procedures may include a clinician physically reviewing the video and/or images and manually labeling objects of interest within the video and/or images. This process is time consuming and monotonous, which increases cost and reduces job satisfaction.

SUMMARY

At least one example embodiment is directed to a device including a memory including instructions, and a processor that executes the instructions to determine, based on eye tracking data, that a clinician gazes at a sub-section of a display for more than a threshold amount of time during a first time period of a medical procedure, where the display displays video of the medical procedure according to a video signal. The processor executes the instructions to identify a block of the video signal that corresponds to the first time period, segment a selected frame in the block of the video signal into a plurality of sub-regions, perform further processing on the plurality of sub-regions, and automatically identify an object of interest within the selected frame based on the further processing.

At least one example embodiment is directed to a system including a display that receives a video signal to display video of a medical procedure being performed by a clinician, an eye tracking device that performs eye tracking of the clinician during the medical procedure to output eye tracking data, a memory including instructions, and a processor that executes the instructions. The processor executes the instructions to determine, based on the eye tracking data, that the clinician gazes at a sub-section of the display for more than a threshold amount of time during a first time period of the medical procedure, identify a block of the video signal that corresponds to the first time period, segment selected frame in the block of the video signal into a plurality of sub-regions, perform further processing on the plurality of sub-regions, and automatically identify an object of interest within the selected frame based on the further processing.

At least one example embodiment is directed to a method that includes determining, based on eye tracking data, that a clinician gazes at a sub-section of a display for more than a threshold amount of time during a first time period of a medical procedure, where the display displays video of the medical procedure according to a video signal. The method includes identifying a block of the video signal that corresponds to the first time period, segmenting selected frame in the block of the video signal into a plurality of sub-regions, performing further processing on the plurality of sub-regions, and automatically identifying an object of interest within the selected frame based on the further processing.

DETAILED DESCRIPTION

Related art approaches for identifying features within medical imagery require manual identification of the features within images, such as concurrent explicit identification by a clinician during a medical procedure, which fundamentally disrupts ordinary medical flow. In addition, post-operative examination and labeling of imagery requires transferring large files of video streams, and may result in a loss of understanding of the immediate medical context, which makes the process time consuming and expensive.

At least one example embodiment proposes to address these and other shortcomings of the related art by using techniques for automatic acquisition of and presumptive labeling of features of interest within medical (e.g., endoscopic) imagery based on observation of sustained clinician visual attention ("gaze"), automated object segmentation techniques, and/or procedural context and secondary cues. The automatic labeling is facilitated by a collection of training data, (e.g., the labeled image data sets trained by deep neural networks) to accurately identify features or conditions in medical imagery.

At least one example embodiment is directed to i) detection of a clinician's sustained visual attention ("gaze") directed at a region of an image on a display (e.g., using an eye tracker or other known method for tracking gaze), ii) baseline analysis/segmentation of the image into primitive "object" regions using image processing and/or artificial intelligence techniques, iii) determination of which, if any, of the segmented object regions appears to be the subject of the clinician gaze via calculation of proximity/intersection of each segmented object region with the clinician's region of visual attention on the display, iv) confirmation that the image is of likely procedural interest by consideration of various surrounding cues (including but not limited to: proximal presence of tooling in the image, concurrent activation of related tooling (e.g. electrosurgery devices), recognized voice annotation by the clinician), and v) capture of an "interesting" image and boundaries of the "segmented object" as a candidate for inclusion in a training set.

A system according to at least one example embodiment may include a clinician using a medical imaging device and/or other medical tooling to perform a medical procedure on an admitted patient. In one example, the medical imaging device is an endoscope. A display presents the live image captured by the endoscope inside the body cavity to enable the clinician to observe and perform the procedure. An eye tracker or equivalent device is used to monitor which part of the display the clinician is looking at throughout the medical procedure. Whenever sustained clinician visual attention to a specific region of the display is detected, the presented image is processed through computer vision object detection or other algorithms to automatically segment the image into candidate "object" regions. The object regions are tested against the region of clinician interest to determine which, if any, object region is judged to be the focus of clinician interest. When a clean association is made, the associated image is archived along with the detected bounds of the segmented "object." Further analysis, based on concurrent usage of related medical tooling and/or other confirmation of clinician interest (e.g., audio utterances) may be used to assign a likelihood of value to the image.

Figure 1:
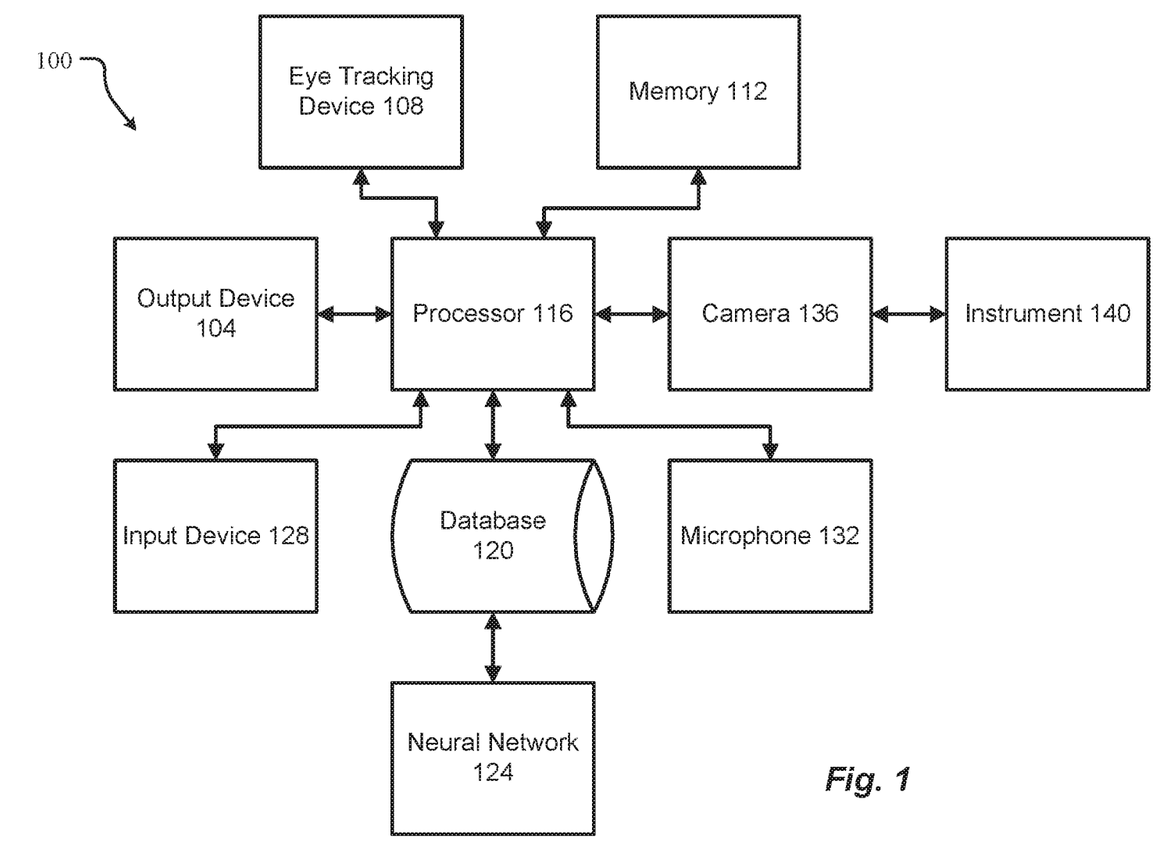
FIG. 1 illustrates a system according to at least one example embodiment.

FIG. 1 illustrates a system 100 according to at least one example embodiment. The system 100 includes an output device 104, an eye tracking device 108, a memory 112, a processor 116, a database 120, a neural network 124, an input device 128, a microphone 132, a camera 136, and an instrument or tooling 140 (e.g., a medical instrument).

The output device 104 may include a display, such as a liquid crystal display (LCD), a light emitting diode (LED) display, or the like. The output device 104 may be a stand-alone display or a display integrated as part of another device, such as a smart phone, a laptop, a tablet, and/or the like. Although a single output device 104 is shown, the system 100 may include more output devices 104 according to system design.

The eye tracking device 108 includes known hardware and/or software capable of tracking eyes of a user within the system 100. For example, the eye tracking device 108 may be an optical eye tracking device that includes a camera, for example, an infrared camera that measures reflections (e.g., corneal reflections) from eyes of a user to determine a gaze of the user. Thus, the eye tracking device 108 may further include a light source, for example, an infrared light source that emits infrared light toward the user in order to create reflection of the infrared light from the user's eyes that is measured by the camera. The eye tracking device 108 may be head-mounted on the user and/or spaced apart at a distance from the user. The eye tracking device 108 may further include processing capability to process reflections from the user's eyes to determine the gaze of the user. Although optical eye tracking is described above, the eye tracking device 108 may employ any known devices and/or methods for eye tracking/gaze detection according to design preferences.

The memory 112 may be a computer readable medium including instructions that are executable by the processor 116. The memory 112 may include any type of computer memory device, and may be volatile or non-volatile in nature. In some embodiments, the memory 112 may include a plurality of different memory devices. Non-limiting examples of memory 112 include Random Access Memory (RAM), Read Only Memory (ROM), flash memory, Electronically-Erasable Programmable ROM (EEPROM), Dynamic RAM (DRAM), etc. The memory 112 may include instructions that enable the processor 120 to control the various elements of the system 100 and to store data, for example, into the database 120 and retrieve information from the database 120. The memory 112 may be local (e.g., integrated with) the processor 116 and/or separate from the processor 116.

The processor 116 may correspond to one or many computer processing devices. For instance, the processor 116 may be provided as a Field Programmable Gate Array (FPGA), an Application-Specific Integrated Circuit (ASIC), any other type of Integrated Circuit (IC) chip, a collection of IC chips, a microcontroller, a collection of microcontrollers, or the like. As a more specific example, the processor 116 may be provided as a microprocessor, Central Processing Unit (CPU), or plurality of microprocessors that are configured to execute the instructions sets stored in memory 112. The processor 116 enables various functions of the system 100 upon executing the instructions stored in memory 112.

The database 120 includes the same or similar structure as the memory 112 described above. In at least one example embodiment, the database 120 is included in a remote server and stores training data for training the neural network 124. The training data contained in the database 120 and used for training the neural network 124 is described in more detail below.

The neural network 124 may be an artificial neural network (ANN) implemented by one or more computer processing devices that are capable of performing functions associated with artificial intelligence (AI) and that have the same or similar structure of the processor 116 executing instructions on a memory having the same or similar structure as memory 112. For example, the neural network 124 uses machine learning or deep learning to improve the accuracy of a set of outputs based on sets of inputs (e.g., similar sets of inputs) over time. As such, the neural network 124 may utilize supervised learning, unsupervised learning, reinforcement learning, self-learning, and/or any other type of machine learning to produce a set of outputs based on a set of inputs. Roles of the neural network 124 are discussed in more detail below. Here, it should be appreciated that the database 120 and the neural network 124 may be implemented by a server or other computing device that is remote from the remaining elements of the system 100.

The input device 128 includes hardware and/or software that enables user input to the system 100. The input device 128 may include a keyboard, a mouse, a touch-sensitive pad, touch-sensitive buttons, mechanical buttons, switches, and/or other control elements for providing user input to the system 100 to enable user control over certain functions of the system 100.

The microphone 132 includes hardware and/or software for enabling detection/collection of audio signals within the system 100. For example, the microphone 132 enables collection of a clinician's voice, activation of medical tooling (e.g., the medical instrument 140), and/or other audio within an operating room.

The camera 136 includes hardware and/or software for enabling collection of video of a medical procedure. In at least one example embodiment, the camera 136 captures video and/or still images of a medical procedure being performed on a body of patient. As is known in endoscopy, arthroscopy, and the like, the camera 136 may be designed to enter a body and take real-time video of the procedure to assist the clinician with performing the procedure and/or making diagnoses. In at least one other example embodiment, the camera 136 remains outside of the patient's body to take video of an external medical procedure. More cameras 136 may be included according to system design.

The instrument or tooling 140 may be a medical instrument or medical tooling that is able to be controlled by the clinician to assist with carrying out a medical procedure on a patient. The camera 136 may be integrated with the instrument 140, for example, in the case of an endoscope. However, example embodiments are not limited thereto, and the instrument 140 may be separate from the camera 136 depending on the medical procedure. Although one instrument 140 is shown, additional instruments 140 may be present in the system 100 depending on the type of medical procedure. In addition, it should be appreciated that the instrument 140 may be for use on the exterior and/or in the interior of a patient's body.

Although FIG. 1 illustrates the various elements in the system 100 as being separate from one another, it should be appreciated that some or all of the elements may be integrated with each other if desired. For example, a single desktop or laptop computer may include the output device 104 (e.g., display), the eye tracking device 108, the memory 112, the processor 116, the input device 128, and the microphone 132. In another example, the neural network 124 may be included with the processor 116 so that AI operations are carried out locally instead of remotely.

It should be further appreciated that each element in the system 100 includes one or more communication interfaces that enable communication with other elements in the system 100. These communication interfaces include wired and/or wireless communication interfaces for exchanging data and control signals between one another. Examples of wired communication interfaces/connections include Ethernet connections, HDMI connections, connections that adhere to PCI/PCIe standards and SATA standards, and/or the like. Examples of wireless interfaces/connections include Wi-Fi connections, LTE connections, Bluetooth connections, NFC connections, and/or the like.

Figure 2:
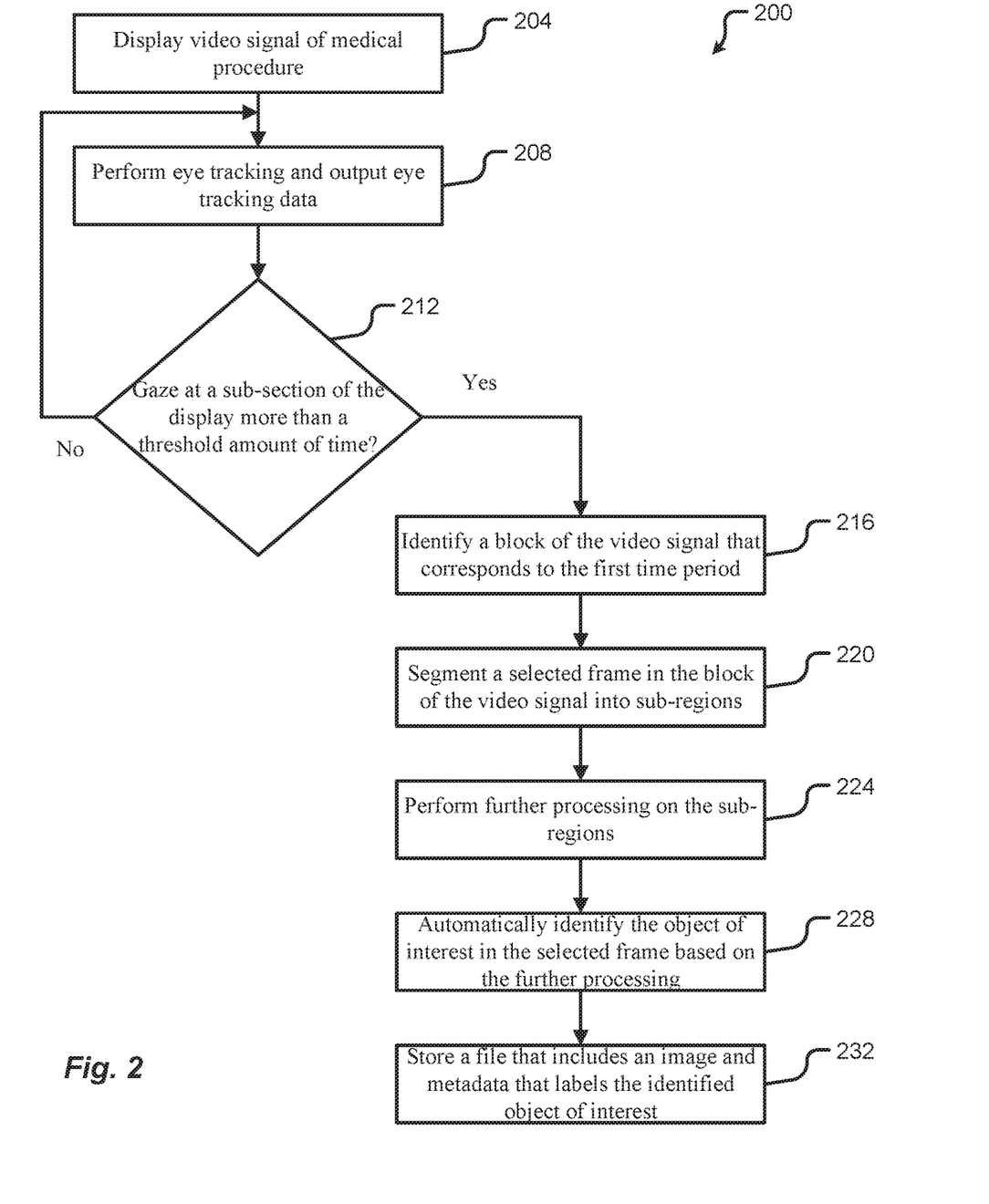
FIG. 2 illustrates a method according to at least one example embodiment.

FIG. 2 illustrates a method 200 according to at least one example embodiment. In general, the method 200 may be performed by one or more of the elements from FIG. 1. For example, some aspects of the method 200 are controlled by the processor 116 while other aspects of the method 200 are performed by other elements in FIG. 1 at the direction of the processor 116.

In operation 204, the method includes a display receiving a video signal to display video of a medical procedure being performed by a clinician. The display may correspond to or be included with the output device 104 in FIG. 1, and the video signal may be captured by the camera 136.

In operation 208, the method includes the eye tracking device 108 conducting eye tracking of the clinician performing the medical procedure that is displayed on the display. The eye tracking device 108 outputs eye tracking data that indicates where the clinician's eyes are focused on the display. As noted above, any suitable eye tracking technology may be used.

In operation 212, the method determines, based on the eye tracking data, whether the clinician gazes at a sub-section of the display for more than a threshold amount of time during a first time period of the medical procedure. If not, the method 200 returns to operation 208. If so, the method 200 proceeds to operation 216. A gaze may be defined as the clinician focusing on a particular region of the display for more than the threshold amount of time as indicated by the eye tracking data. The threshold amount of time may be a design parameter set based on empirical evidence and/or preference (e.g., 1 s, 2 s, or 5 s). The bounds of the particular region on which the clinician focuses before a gaze is detected may also be a design parameter set based on empirical evidence and/or preference. That is, a gaze may be detected so long as the clinician's eyes remain focused on a region of the display, where the region of the display is variable so as to allow for at least some eye movement while still detecting a gaze.

In operation 216, the method identifies a block of the displayed video signal that corresponds to the first time period. For example, in the event that the video of the medical procedure is recorded in memory 112, the processor 116 accesses the memory 112 and locates the block of the video signal using time stamps. For example, the processor 116 may record a time stamp of when the clinician gaze was detected, and locate a corresponding time stamp on a frame of the recorded video signal and use that frame as the block of video that corresponds to the first time period. In at least one other example, the processor 116 locates the corresponding time stamp on a frame of the video signal and then the processor 116 identifies frames that have a set of time stamps before and/or after the corresponding time stamp as the block of video that corresponds to the first time period. The number of time stamps (or frames) identified before and/or after the corresponding time stamps (or frame) may be a design parameter set based on empirical evidence and/or preference.

In at least one other example embodiment, the processor 116 starts a timer when a partial gaze is detected, and if the timer expires before the gaze changes, the processor 116 detects a full gaze and considers the first time period to be the time between when the timer started and expired. In this case, the threshold amount of time for detecting the full gaze includes the threshold amount of time for detecting the partial gaze.

Although identifying the block of the video signal using time stamps is discussed above, other methods are possible should be readily understood in view of the above explanation.

In operation 220, the method segments a selected frame (e.g., an image) in the block of the video signal into a plurality of sub-regions using, for example, image segmentation techniques with or without semantic awareness. For example, the processor 116 segments the selected frame using known edge detection methods that detect edges of objects within the selected frame. In this case, each sub-region may correspond to an object or part of an object within the selected frame. Other image segmentation methods/algorithms are possible depending on design choice. Here, it should be appreciated that the processor 116 may segment the entire selected frame or only a portion of the selected frame into sub-regions. For example, if desired, the processor 116 may segment only the portion of the selected frame that corresponds to the region of clinician's focus on the display, which saves processing resources (see operation 300 in FIG. 3).

In operation 224, the method performs further processing on the plurality of sub-regions. The further processing is discussed in more detail below with reference to FIG. 3. Here, it should be appreciated that the method may bypass the further processing on blocks of the video signal that do not correspond to the first time period. That is, the processor 116 bypasses the further processing in operation 224 for frames of the video signal that do not correspond to time periods where the gaze of the clinician was detected, thereby conserving computing resources.

In operation 228, the method automatically identifies an object of interest within the selected frame based on the further processing. The object of interest may correspond to an object within a region of the selected frame that corresponds to a region on display that received the clinician's gaze in operation 212. Examples of objects of interest include objects that are suspected tumors, polyps, arteries, lesions, ligaments, bones, abnormal growths, dermatological abnormalities, and/or the like. In one example, the processor 116 may automatically identify the object of interest based on output from the neural network 124, which has been trained to recognize similar objects of interest from other similar medical procedures and/or models of similar objects.

In the event that the neural network 124 is not sufficiently trained, unavailable, or not desired to be used, automatic recognition of the object of interest may include the processor 116 carrying out one or more object detection/recognition algorithms, for example, a scale-invariant feature transform (SIFT) algorithm. Additionally or alternatively, the processor 116 may compare boundaries of the sub-regions from operation 220 to boundaries of other known objects in the database 120 (or memory 112). If the correlation between boundaries of the object of interest and a known object from the database 120 exceeds a preset threshold, the processor 116 treats the correlation as a match and labels the object of interest with the label of the known object. Here, it should be appreciated that the method (through the processor 116 and/or neural network 124) may use any known method for identifying the object of interest based on previously identified objects of interest with the same or similar characteristics.

In operation 232, the method stores a file (e.g., in the database 120 and/or memory 112). For example, the processor 116 stores a file that includes an image of the selected frame and metadata that labels the identified object of interest from operation 228 on the image (see FIG. 7). The metadata may appear in the image in a manner that associates the label with the identified object of interest. For example, the metadata may include a label with a physical pointer or arrow to the object and/or color coding where the label and a boundary of the object have a same color, and/or the like. Additionally or alternatively, the label may be placed in proximity to the object so as to be easily associated with the object by a viewer. In at least one example embodiment, the processor 116 stores the file with a filename that is indicative of characteristics associated with the image and/or metadata. For example, the filename may include text that indicates the type of object(s) labeled within the image, text to indicate the type, date, and/or location of the medical procedure, and/or other characters/numbers that would be useful for distinguishing the file from other files when performing a search function or visual inspection of the filename. Additionally, the processor 116 may automatically create a folder associated with a single medical procedure and place all images from the medical procedure into the folder.

Here, it should be understood that operations 224, 228, and 232 may be carried out for additional objects of interest within the selected frame if desired.

Figure 3:
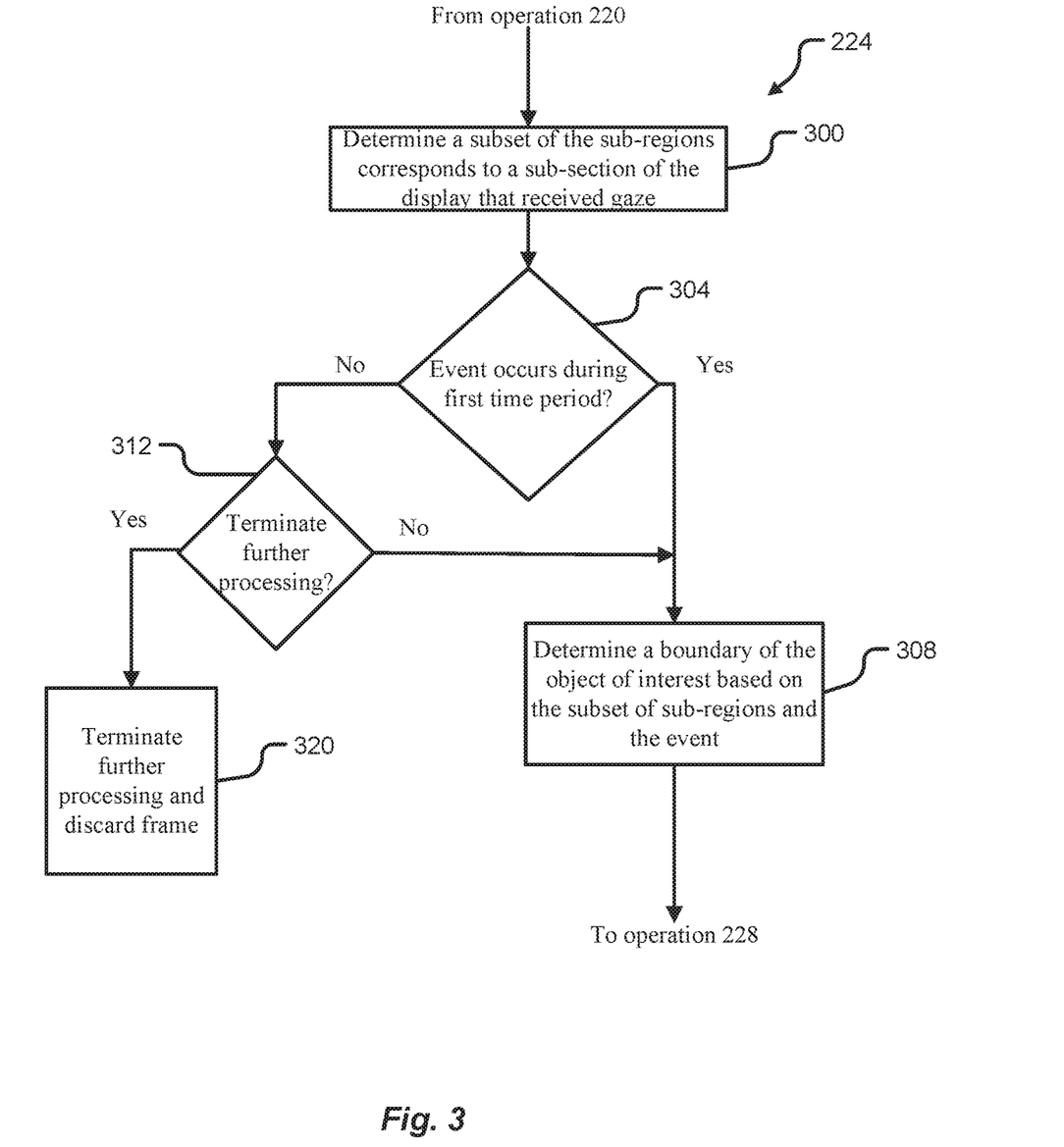
FIG. 3 illustrates additional details for the method in FIG. 2 according to at least one example embodiment.

FIG. 3 illustrates additional details for the method 200 in FIG. 2 according to at least one example embodiment. In particular, FIG. 3 shows operations that may occur within or instead of operation 224 of FIG. 2.

In operation 300, the method determines a subset of the plurality of sub-regions from operation 220 that corresponds to a sub-section of the display that received the clinician's gaze in operation 212. For example, given known factors of the display and the camera 236 (e.g., pixel counts, resolutions, etc.), the processor 116 may translate coordinates of the region of the display that received the clinician's gaze into coordinates within the selected frame (or image) in the block of video. Here, it should be appreciated that operation 300 conserves computing resources by segmenting only a portion of the frame that corresponds to the region of clinician's focus on the display. Thus, operation 300 is an optional operation for the further processing operation 224.

In operation 304, the method determines whether an event occurs during the first time period or in proximity to the first time period referred to in operation 216. In general, events are occurrences within the medical procedure that may assist with confirming that the selected frame operated on in operation 220 is of procedural interest, and that the selected frame should be further processed and stored in operations 228 and 232. Examples of events are described in more detail with reference to FIG. 6 and may include activation of tooling used during the medical procedure, voice annotation of the medical procedure (e.g., by the clinician), and the presence of tooling used during the medical procedure in the selected frame. That is, detection of an event within the first time period or within proximity of the first time period (i.e., within some desired threshold amount of time before and/or after the first time period) may also be an indicator that there is an object of interest on the display. Thus, detecting the clinician's gaze in conjunction with detecting one or more events increases the likelihood that the block of video contains an object of interest that should be identified, labeled, and stored (e.g., for future use in a training data set for the neural network 124).

If, in operation 304, the method detects that an event occurs during the first time period, the method proceeds to operation 308 and determines a boundary of the object of interest in the selected frame based on the subset of the plurality of sub-regions and the at least one event. Consider an example where medical procedure is a colonoscopy and the event is the clinician or other medical technician uttering a keyword, such as "polyp," picked up by the microphone 132. Upon detecting that "polyp" has been uttered in combination with detecting that a gaze has occurred at a particular region of the display, the processor 116 attempts to identify boundaries of objects in the particular region that may correspond to a polyp. Specifically, the processor 116 may identify one or more boundaries within the subset of sub-regions determined in operation 300 based on output from the neural network 124 and/or other apriori knowledge of the shapes of polyps.

In at least one other example, the processor 116 does not necessarily attempt to use the event to generate specific boundaries, and may consider the detection of an event as a trigger for proceeding to general boundary determination in operation 308. In this manner, the occurrence of an event generally assists with ensuring that boundary detection occurs on frames that more likely to contain an object of interest than frames that did not have an associated event. General boundary determination may occur in accordance with known algorithms and methods. Operation 308 may further include the processor 116 combining certain ones of the subset of the sub-regions in order to generate the boundary for the object of interest. In other words, the processor 116 may combine neighboring sub-regions that have a selected range of pixel values and determine a boundary for the combined sub-regions.

After operation 308, the processor 116 continues with operation 228 in FIG. 2.

If, in operation 304, the method detects that an event did not occur within the first time period, the method proceeds to operation 312 and determines whether to terminate further processing. The decision to terminate further processing may be based on user input that was programmed in advance or that occurs in real-time. For example, the processor 116 may be executing an application with a user interface that allows the clinician (or other entity) to select whether or not further processing should be terminated when no event is detected in operation 304. This provides the user with the ability to ignore event detection if desired, and proceed with processing the frame when only a gaze is detected. Additionally or alternatively, the decision in operation 312 may be based current usage of computing resources. If there are sufficient computing resources, the processor 116 may proceed to operation 308, and if not, the processor 116 may terminate the further processing in operation 320.

If the further processing is not terminated in operation 312, the method proceeds to operation 308, described above. If the further processing is terminated in operation 312, the method proceeds to operation 320 where, for example, the processor 116 terminates processing (i.e., does not perform operations 228 and 232 in FIG. 2) and discards the frame (e.g., deletes the frame from temporary memory).

Figure 4:
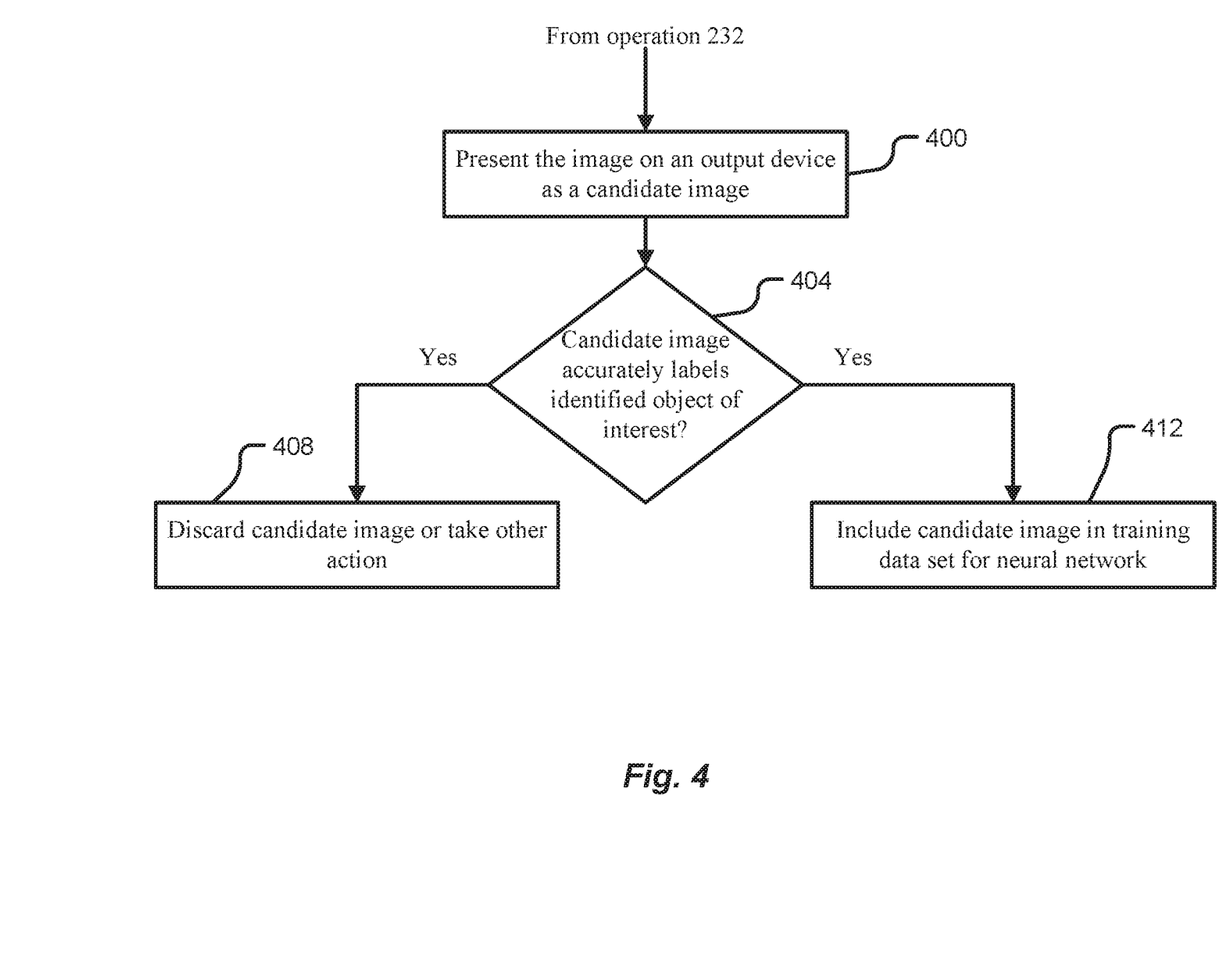
FIG. 4 illustrates a method that may be carried out in addition to the method of FIG. 2 according to at least one example embodiment.

FIG. 4 illustrates a method that may be carried out with the method of FIG. 2 according to at least one example embodiment. For example, operation 232 in FIG. 2 may proceed to operation 400 in FIG. 4. In operation 400, the method may present the image. For example, the processor 116 presents the image that includes the object of interest and the metadata that labels the object of interest on the output device 104 as a candidate image that may be included in a training data set for the neural network 124.

In operation 404, the method determines whether the candidate image contains accurate labels for the identified object of interest. For example, the processor 116 receives user input (e.g., clinician input) from a user interface of an application that is rendering the image that indicates whether the label of the object of interest is accurate. If not, the processor 116 may discard the candidate image by deleting the candidate image from memory, or take other action. For example, the processor 116 may take other action by requesting feedback from the user as to an accurate label for the object of interest in the candidate image. The feedback may be audio in nature (e.g., a clinician's voice) and/or tactile in nature (e.g., input on a keyboard or mouse). The processor 116 may then consider the candidate image with the corrected label as being an accurately labeled image for inclusion into a training data set (i.e., for operation 412). In addition, the processor 116 may use the feedback and/or send the feedback to neural network 124 to avoid mislabeling similar objects of interest in other images.

If the candidate image is determined to be accurately labeled in operation 404, the method proceeds to operation 412 and includes the candidate image in a data set for training the neural network 124. For example, the processor 116 sends the file with the candidate image to the database 120 for storage. The file with the candidate image may then be accessed by the neural network 124 along with other files for training purposes and/or for identifying other objects. Thus, the system may provide a recommendation on an identity of the another object of interest in another medical procedure based on the files now including the candidate image from operation 412.

Here, it should be appreciated that the operations in FIGS. 2, 3, and 4 do not necessarily have to be performed in the order shown and described. For example, operations involving event detection in FIG. 3 may occur prior to segmentation in operation 220 if desired, which may conserve computing resources if an event is not detected and processing is terminated to avoid using computing resources on the segmentation in operation 220. One skilled in the art should appreciate that other operations within FIGS. 2-4 may be reordered according to design preferences.

Figure 5:
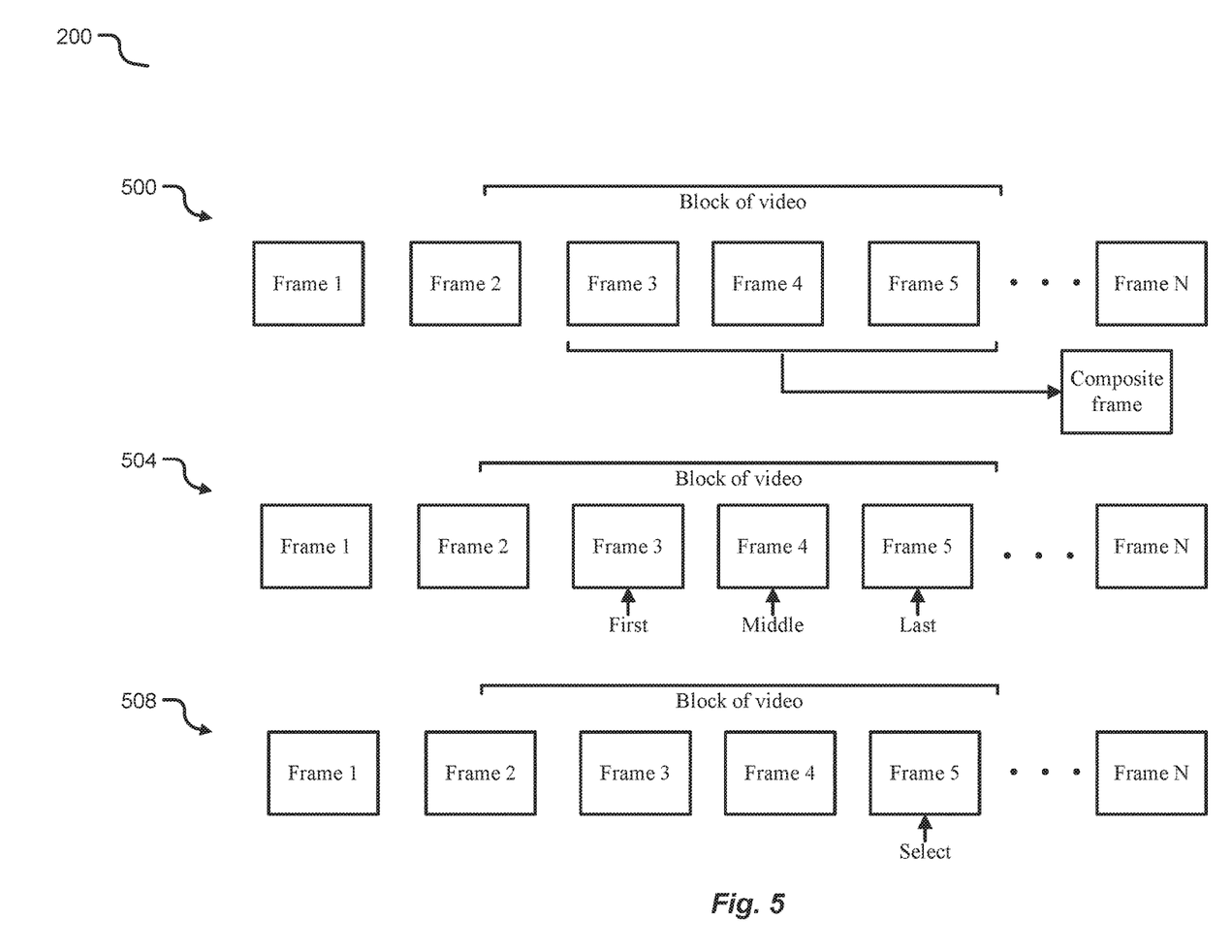
FIG. 5 illustrates options for selecting and/or generating a selected frame according to at least one example embodiment.

FIG. 5 illustrates options for selecting and/or generating a frame according to at least one example embodiment. The selected and/or generated frame is then segmented in accordance with the operations described above in FIGS. 2 and 3. In more detail, FIG. 5 shows options for selecting a frame, where each option illustrates a video signal 500, 504, and 508 captured by the camera 236 during the medical procedure that corresponds to a different manner of selecting or generating a frame that is segmented in operation 220 from FIG. 2. In general, the video signals 500, 504, 508 include first through Nth frames. FIG. 5 illustrates blocks of video as multiple frames that are time sequential and that are identified according to operation 216 from FIG. 2. A number of frames within the block of video may vary according to a frame rate of the video signal and a length of the first time period as determined in the discussion of FIG. 2. FIG. 5 illustrates an example where the block of video in each video signal 500, 504, and 508 covers three full frames, frames 3, 4, and 5.

The video signal 500 illustrates an example of generating the selected frame as a composite frame from frames 3, 4, and 5. The processor 116 may generate the composite frame by averaging respective pixel values in each of the frames 3, 4, and 5 and producing the composite frame as a single frame with the averaged pixel values. However, example embodiments are not limited thereto, and the composite frame may be generated according to any known method for combining multiple frames and/or images into a single frame/image. In addition, although the composite frame in this example is generated based on all frames in the block of video, the composite frame may be generated using any number of frames in any position within the block of video.

The video signal 504 illustrates an example of determining the selected frame based on the frame position within the block of video. For example, the processor 116 may be programmed to select the first, middle, or last full frame within the block of video depending on design preferences.

The video signal 508 illustrates an example of selecting a specific frame based on clinician input and/or based on other factors. In the case of clinician input, frame 5 may be selected as the selected frame for segmentation as a result of the clinician instructing the camera 236 to capture a still image during the medical procedure. As may be the case in a camera assisted medical procedure, the camera 236 may takes video of the procedure but is also controllable to take still images during the procedure, for example, by the clinician pressing a button or taking other action (e.g., a voice command) that causes the camera 236 to take a still image and/or that causes the processor 116 to mark the frame of the video signal at the time of pressing the button or taking other action.

In at least one example embodiment, the processor 116 automatically determines the selected frame based on other factors by examining at least some of the frames in the block of video for artifacts, motion blur, and/or other image quality defects, and determines the selected frame as the frame with the best image quality.

In at least one other example embodiment, the clinician selection and automatic selection may be combined such that a frame selected by the clinician via a button press is examined by the processor 116 for defects and compared to other frames within the block of video. In the event that the processor 116 determines that a different frame in the block of video contains the same or similar objects as the frame selected by the clinician and also possesses better image quality or characteristics more favorable for image processing, the processor 116 may select the frame with the better image quality or more favorable characteristics.

In the examples of FIG. 5, it should be appreciated that the selected frame is selected or generated from among frames that are fully contained within the block of video. However, example embodiments are not limited thereto, and frames that are not fully covered by the block of video (e.g., frame 2 in FIG. 5) may be included in the selection and/or generation of the selected frame if desired.

Figure 6:
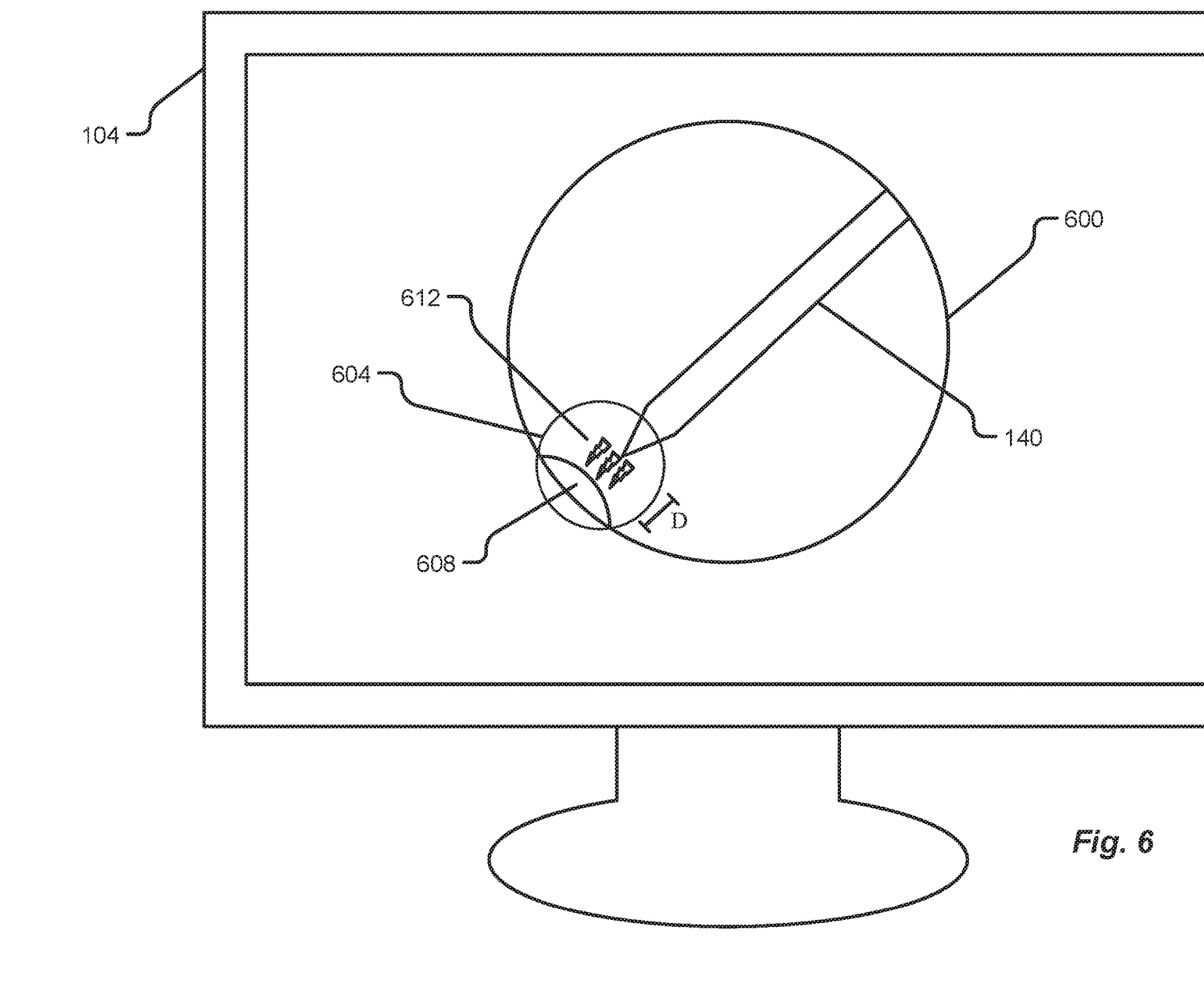
FIG. 6 illustrates examples of events according to at least one example embodiment.

FIG. 6 illustrates examples of events according to at least one example embodiment. As noted above, events are occurrences within the medical procedure may assist with confirming that the selected frame segmented in operation 220 is of procedural interest, and that the selected frame should be further processed and stored in operations 228 and 232. The discussion of FIG. 3 sets forth an example where the event is an audio utterance or voice annotation of the medical procedure by, for example, the clinician. Other examples of events include activation of tooling used during the medical procedure and presence of tooling used during the medical procedure in the selected frame. However, these are just examples of events and other events are within the scope of inventive concepts.

In more detail, FIG. 6 shows the output device 104 as a display that depicts a frame of a video signal or image of a medical procedure captured by camera 236. FIG. 6 will be discussed with respect to the example of an endoscopy of an esophagus having an esophageal wall 600. FIG. 6 illustrates a region of interest (ROI) 604 that has received the clinician's gaze as detected by the eye tracking device 108 and as described in operation 212 of FIG. 2. The ROI 604 includes an object of interest 608, which in this example is a possible abnormality on the esophageal wall 600 (e.g., a growth).

In order to confirm that the frame depicted in FIG. 6 should be processed further, methods according to example embodiments detect events as described in FIG. 3. One possible event is the mere presence of the instrument or tooling 140 within the frame. Another possible event is the instrument 140 being moved by the clinician within a threshold distance D of the object of interest 608, where the threshold distance is a design parameter set based on empirical evidence and/or preference. Still another possible event is activation 612 of the instrument or tooling 140, which in this example may include activation of an electrosurgical device designed to remove or treat the growth on the wall 600. Yet another event is the entry of the instrument 140 into the ROI 608. Another example of an event is a location of the camera 236 within the esophagus, which may account for situations where certain abnormalities are known to occur within a particular section of the region being examined. The number and type of events may depend on the type of medical procedure, and should be appreciated by those skilled in the art as being within the scope of inventive concepts.

In cases where multiple events are detected by the system for a video block, the system may assign more importance or value to the corresponding selected frame than if only a single event is detected, which may be useful for post-operation examination of many files generated and stored according to example embodiments. For example, the files with presumed higher values (i.e., more detected events) may be presented to the clinician before the files with lower values. In addition, the metadata on the image stored in operation 232 may include descriptions of the type of event(s) detected when the video block was identified in operation 216.

Figure 7:
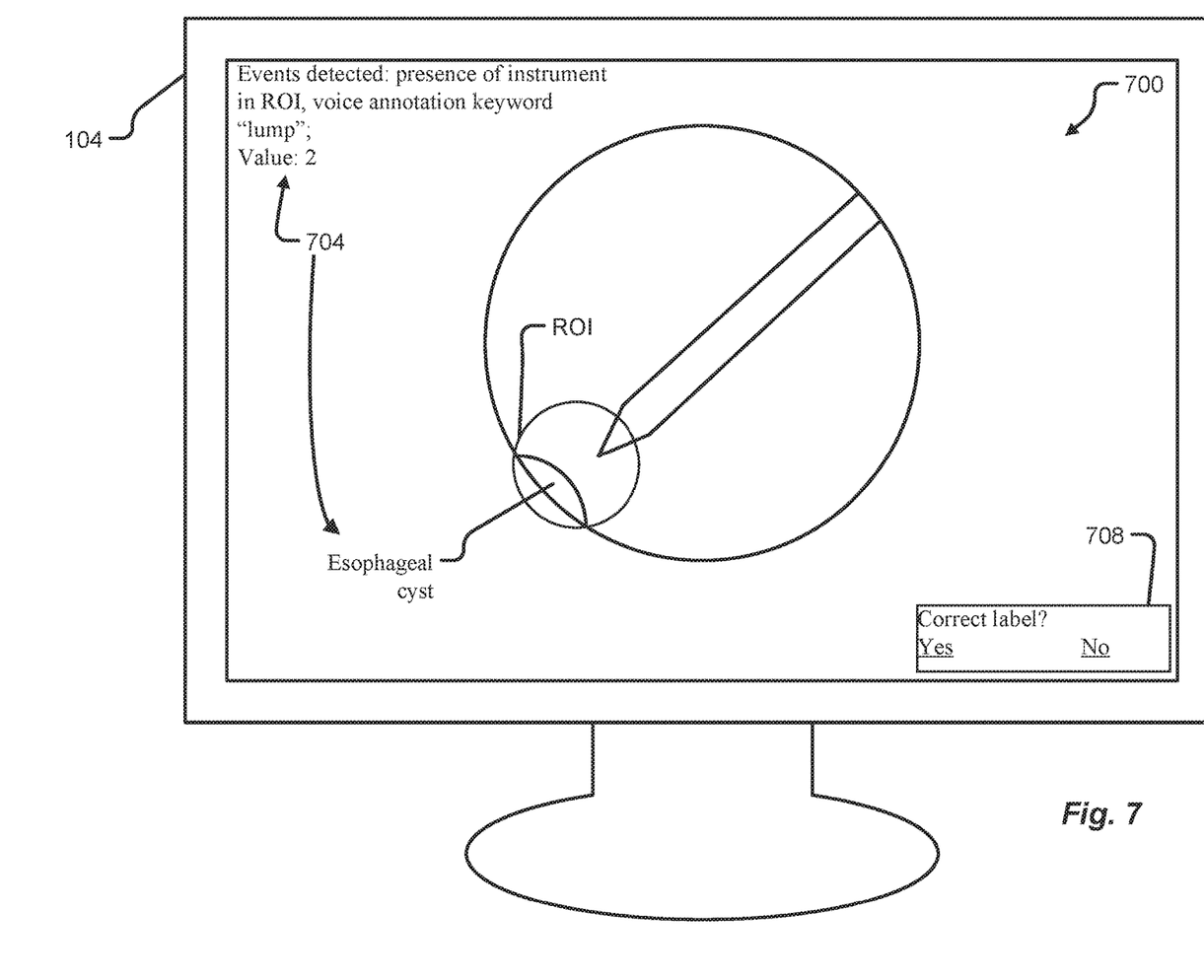
FIG. 7 illustrates a presentation of an image generated according to example embodiments.

FIG. 7 illustrates a presentation of an image generated according to example embodiments. The image 700 is displayed on the output device 104 and includes metadata 704 and a user input field 708. The image 700 may correspond to an image presented in operation 400 based on a medical procedure that involved the esophagus example in FIG. 6. As noted above, the metadata 704 labels the object of interest 608 in FIG. 6 as an esophageal cyst in the ROI, and includes a description of events detected and an assigned value that, in this case, corresponds to the number of events detected (which may in turn correspond to an importance or value of the image to the clinician). The metadata 704 including the label is generated in accordance with example embodiments described above. The user input field 708 may be part of an application with a user interface that assists the clinician with determining whether to use the image 700 as training data for the neural network 124. As noted above, the clinician or other evaluator can select "yes" or "no" to verify whether the automatically assigned label "esophageal cyst" is correct before carrying out other operations described with reference to FIG. 4.

Although example embodiments have been described with respect to medical procedures that occur internal to a patient, example embodiments may also be applied to medical procedures that generally occur external to a patient or for any non-medical procedure that is camera assisted (e.g., in manufacturing, food processing, etc.).

In view of foregoing description, it should be appreciated that example embodiments provide efficient methods for automatically identifying and labeling objects of interest within images of a medical procedure, which may then be presented to a clinician as candidate images for inclusion into a data set intended to train a neural network or other AI network. Methods and devices according to example embodiments save time, cost, and computational resources compared to the related art.

At least one example embodiment is directed to a device including a memory including instructions, and a processor that executes the instructions to determine, based on eye tracking data, that a clinician gazes at a sub-section of a display for more than a threshold amount of time during a first time period of a medical procedure, where the display displays video of the medical procedure according to a video signal. The processor executes the instructions to identify a block of the video signal that corresponds to the first time period, segment a selected frame in the block of the video signal into a plurality of sub-regions, perform further processing on the plurality of sub-regions, and automatically identify an object of interest within the selected frame based on the further processing.

According to at least one example embodiment, the selected frame includes multiple frames that are sequential in time.

According to at least one example embodiment, the selected frame is a composite frame of the multiple frames generated by averaging respective pixel values in each of the multiple frames.

According to at least one example embodiment, the selected frame is a first, middle, or last frame in the multiple frames.

According to at least one example embodiment, the processor executes the instructions to receive clinician input and select the selected frame based on the clinician input.

According to at least one example embodiment, the processor executes the instructions to bypass the further processing on blocks of the video signal that do not correspond to the first time period.

According to at least one example embodiment, the processor performs the further processing to determine that a subset of the plurality of sub-regions corresponds to the sub-section of the display.

According to at least one example embodiment, the processor performs the further processing to determine that at least one event associated with the medical procedure occurred during the first time period or in proximity to the first time period.

According to at least one example embodiment, the at least one event includes activation of tooling used during the medical procedure, voice annotation of the medical procedure, or a presence of tooling used during the medical procedure in the selected frame, or any combination thereof.

According to at least one example embodiment, the processor performs the further processing to determine a boundary of the object of interest in the selected frame based on the subset of the plurality of sub-regions and the at least one event.

According to at least one example embodiment, the processor automatically identifies the object of interest based on a comparison of the boundary of the object of interest to one or more boundaries of one or more other objects in a database.

According to at least one example embodiment, the processor executes the instructions to store a file in a database that includes an image corresponding to the selected frame and metadata that labels the identified object of interest on the image.

According to at least one example embodiment, the file is one of a plurality of files stored in the database that are accessed to train a neural network on identifying another object of interest.

According to at least one example embodiment, the processor executes the instructions to use output of the neural network trained with the plurality of files, and to provide a recommendation on an identity of the another object of interest in another medical procedure based on the plurality files.

According to at least one example embodiment, the processor executes the instructions to receive feedback on the recommendation that is used to train the neural network.

According to at least one example embodiment, the feedback includes audio feedback or tactile feedback from the clinician.

At least one example embodiment is directed to a system including a display that receives a video signal to display video of a medical procedure being performed by a clinician, an eye tracking device that performs eye tracking of the clinician during the medical procedure to output eye tracking data, a memory including instructions, and a processor that executes the instructions. The processor executes the instructions to determine, based on the eye tracking data, that the clinician gazes at a sub-section of the display for more than a threshold amount of time during a first time period of the medical procedure, identify a block of the video signal that corresponds to the first time period, segment selected frame in the block of the video signal into a plurality of sub-regions, perform further processing on the plurality of sub-regions, and automatically identify an object of interest within the selected frame based on the further processing.

According to at least one example embodiment, the processor executes the instructions to store a file in a database that includes an image corresponding to the selected frame and metadata that labels the identified object of interest on the image, and present the image and the metadata on an output device as a candidate image.

According to at least one example embodiment, the processor executes the instructions to receive input that confirms the candidate image accurately labels the identified object of interest, and include the candidate image in a data set used to train the neural network to identify the other objects of interest.

At least one example embodiment is directed to a method that includes determining, based on eye tracking data, that a clinician gazes at a sub-section of a display for more than a threshold amount of time during a first time period of a medical procedure, where the display displays video of the medical procedure according to a video signal. The method includes identifying a block of the video signal that corresponds to the first time period, segmenting selected frame in the block of the video signal into a plurality of sub-regions, performing further processing on the plurality of sub-regions, and automatically identifying an object of interest within the selected frame based on the further processing.

Any one or more of the aspects/embodiments as substantially disclosed herein.

Any one or more of the aspects/embodiments as substantially disclosed herein optionally in combination with any one or more other aspects/embodiments as substantially disclosed herein.

One or more means adapted to perform any one or more of the above aspects/embodiments as substantially disclosed herein.

The phrases "at least one," "one or more," "or," and "and/or" are open-ended expressions that are both conjunctive and disjunctive in operation. For example, each of the expressions "at least one of A, B and C," "at least one of A, B, or C," "one or more of A, B, and C," "one or more of A, B, or C," "A, B, and/or C," and "A, B, or C" means A alone, B alone, C alone, A and B together, A and C together, B and C together, or A, B and C together.

The term "a" or "an" entity refers to one or more of that entity. As such, the terms "a" (or "an"), "one or more," and "at least one" can be used interchangeably herein. It is also to be noted that the terms "comprising," "including," and "having" can be used interchangeably.

Aspects of the present disclosure may take the form of an embodiment that is entirely hardware, an embodiment that is entirely software (including firmware, resident software, micro-code, etc.) or an embodiment combining software and hardware aspects that may all generally be referred to herein as a "circuit," "module," or "system." Any combination of one or more computer-readable medium(s) may be utilized. The computer-readable medium may be a computer-readable signal medium or a computer-readable storage medium.

A computer-readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer-readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer-readable storage medium may be any tangible medium that can contain or store a program for use by or in connection with an instruction execution system, apparatus, or device.

The terms "determine," "calculate," "compute," and variations thereof, as used herein, are used interchangeably and include any type of methodology, process, mathematical operation or technique.

Example embodiments may be configured according to the following:

(1) A device comprising:
a memory including instructions; and
a processor that executes the instructions to:
determine, based on eye tracking data, that a clinician gazes at a sub-section of a display for more than a threshold amount of time during a first time period of a medical procedure, the display displaying video of the medical procedure according to a video signal;
identify a block of the video signal that corresponds to the first time period;
segment a selected frame in the block of the video signal into a plurality of sub-regions;
perform further processing on the plurality of sub-regions; and
automatically identify an object of interest within the selected frame based on the further processing.

(2) The device of (1), wherein block of the video signal includes multiple frames that are sequential in time.

(3) The device of one or more of (1) to (2), wherein the selected frame is a composite frame of the multiple frames generated by averaging respective pixel values in each of the multiple frames.

(4) The device of one or more of (1) to (3), wherein the selected frame is a first, middle, or last frame in the multiple frames.

(5) The device of one or more of (1) to (4), wherein the processor executes the instructions to receive clinician input and select the selected frame based on the clinician input.

(6) The device of one or more of (1) to (5), wherein the processor executes the instructions to bypass the further processing on blocks of the video signal that do not correspond to the first time period.

(7) The device of one or more of (1) to (6), wherein the processor performs the further processing to determine that a subset of the plurality of sub-regions corresponds to the sub-section of the display.

(8) The device of one or more of (1) to (7), wherein the processor performs the further processing to determine that at least one event associated with the medical procedure occurred during the first time period or in proximity to the first time period.

(9) The device of one or more of (1) to (8), wherein the at least one event includes activation of tooling used during the medical procedure, voice annotation of the medical procedure, or a presence of tooling used during the medical procedure in the selected frame, or any combination thereof.

(10) The device of one or more of (1) to (9), wherein the processor performs the further processing to determine a boundary of the object of interest in the selected frame based on the subset of the plurality of sub-regions and the at least one event.

(11) The device of one or more of (1) to (10), wherein the processor automatically identifies the object of interest based on a comparison of the boundary of the object of interest to one or more boundaries of one or more other objects in a database.

(12) The device of one or more of (1) to (11), wherein the processor executes the instructions to store a file in a database that includes an image corresponding to the selected frame and metadata that labels the identified object of interest on the image.

(13) The device of one or more of (1) to (12), wherein the file is one of a plurality of files stored in the database that are accessed to train a neural network on identifying another object of interest.

(14) The device of one or more of (1) to (13), wherein the processor executes the instructions to use output of the neural network trained with the plurality of files, and to provide a recommendation on an identity of the another object of interest in another medical procedure based on the plurality files.

(15) The device of one or more of (1) to (14), wherein the processor executes the instructions to receive feedback on the recommendation that is used to train the neural network.

(16) The device of one or more of (1) to (15), wherein the feedback includes audio feedback or tactile feedback from the clinician.

(17) A system, comprising:
a display that receives a video signal to display video of a medical procedure being performed by a clinician;
an eye tracking device that performs eye tracking of the clinician during the medical procedure to output eye tracking data;
a memory including instructions;
a processor that executes the instructions to:
determine, based on the eye tracking data, that the clinician gazes at a sub-section of the display for more than a threshold amount of time during a first time period of the medical procedure;
identify a block of the video signal that corresponds to the first time period;
segment selected frame in the block of the video signal into a plurality of sub-regions;
perform further processing on the plurality of sub-regions; and
automatically identify an object of interest within the selected frame based on the further processing.

(18) The system of (17), wherein the processor executes the instructions to:
store a file in a database that includes an image corresponding to the selected frame and metadata that labels the identified object of interest on the image; and
present the image and the metadata on an output device as a candidate image.

(19) The system of one or more of (17) to (18), wherein the processor executes the instructions to:
receive input that confirms the candidate image accurately labels the identified object of interest; and
include the candidate image in a data set used to train the neural network to identify the other objects of interest.

(20) A method, comprising:
determining, based on eye tracking data, that a clinician gazes at a sub-section of a display for more than a threshold amount of time during a first time period of a medical procedure, the display displaying video of the medical procedure according to a video signal;
identifying a block of the video signal that corresponds to the first time period;
segmenting selected frame in the block of the video signal into a plurality of sub-regions;
performing further processing on the plurality of sub-regions; and
automatically identifying an object of interest within the selected frame based on the further processing.

What is claimed is:

1. A device comprising:
a memory including instructions; and
a processor that executes the instructions to:
determine, based on eye tracking data, that a clinician gazes at a sub-section of a display for more than a threshold amount of time during a first time period of a medical procedure, the display displaying video of the medical procedure according to a video signal;
identify a block of the video signal that corresponds to the first time period;
segment a selected frame in the block of the video signal into a plurality of sub-regions;
perform further processing on the plurality of sub-regions including determining that a subset of the plurality of sub-regions corresponds to the sub-section of the display, and determining, in response to determining that the subset of the plurality of sub-regions corresponds to the sub-section of the display, that at least one event associated with the medical procedure occurs during the first time period or in proximity to the first time period to confirm that the subset of the plurality of sub-regions is a region of interest; and
automatically identify an object of interest within the selected frame based on the further processing.

2. The device of claim 1, wherein block of the video signal includes multiple frames that are sequential in time.

3. The device of claim 2, wherein the selected frame is a composite frame of the multiple frames generated by averaging respective pixel values in each of the multiple frames.

4. The device of claim 2, wherein the selected frame is a first, middle, or last frame in the multiple frames.

5. The device of claim 1, wherein the processor executes the instructions to receive clinician input and select the selected frame based on the clinician input.

6. The device of claim 1, wherein the processor executes the instructions to bypass the further processing on blocks of the video signal that do not correspond to the first time period.

7. The device of claim 1, wherein the processor outputs an output image including the object of interest as a candidate image for confirmation as an accurately labeled object of interest.

8. A device comprising;
a memory including instructions; and
a processor that executes the instructions to:
determine, based on eye tracking data, that a clinician gazes at a sub-section of a display for more than a threshold amount of time during a first time period of a medical procedure, the display displaying video of the medical procedure according to a video signal;
identify a block of the video signal that corresponds to the first time period;
segment a selected frame in the block of the video signal into a plurality of sub-regions;
perform further processing on the plurality of sub-regions; and
automatically identify an object of interest within the selected frame based on the further processing, wherein the processor performs the further processing to determine that a subset of the plurality of sub-regions corresponds to the sub-section of the display, and wherein the processor performs the further processing to determine that at least one event associated with the medical procedure occurred during the first time period or in proximity to the first time period.

9. The device of claim 8, wherein the at least one event includes activation of tooling used during the medical procedure, voice annotation of the medical procedure, or a presence of tooling used during the medical procedure in the selected frame, or any combination thereof.

10. The device of claim 8, wherein the processor performs the further processing to determine a boundary of the object of interest in the selected frame based on the subset of the plurality of sub-regions and the at least one event.

11. The device of claim 10, wherein the processor automatically identifies the object of interest based on a comparison of the boundary of the object of interest to one or more boundaries of one or more other objects in a database.

12. The device of claim 1, wherein the processor executes the instructions to store a file in a database that includes an image corresponding to the selected frame and metadata that labels the identified object of interest on the image.

13. A device comprising:
a memory including instructions; and
a processor that executes the instructions to;
determine, based on eye tracking data, that a clinician gazes at a sub-section of a display for more than a threshold amount of time during a first time period of medical procedure, the display displaying video of the medical procedure according to a video signal;
identify a block of the video signal that corresponds to the first time period;
segment a selected frame in the block of the video signal into a plurality of sub-regions;
perform further processing on the plurality of sub-regions; and
automatically identify an object of interest within the selected frame based on the further processing, wherein the processor executes the instruction to store a fie n a database that includes an image corresponding to the selected frame and metadata that labels the identified object of interest on the image, and wherein the file is one of a plurality of files stored in the database that are accessed to train a neural network on identifying another object of interest.

14. The device of claim 13, wherein the processor executes the instructions to use output of the neural network trained with the plurality of files, and to provide a recommendation on an identity of the another object of interest in another medical procedure based on the plurality files.

15. The device of claim 14, wherein the processor executes the instructions to receive feedback on the recommendation that is used to train the neural network.

16. The device of claim 15, wherein the feedback includes audio feedback or tactile feedback from the clinician.

17. A system, comprising:
a display that receives a video signal to display video of a medical procedure being performed by a clinician;
an eye tracking device that performs eye tracking of the clinician during the medical procedure to output eye tracking data;
a memory including instructions;
a processor that executes the instructions to:
determine, based on the eye tracking data, that the clinician gazes at a sub-section of the display for more than a threshold amount of time during a first time period of the medical procedure;
identify a block of the video signal that corresponds to the first time period;

segment selected frame in the block of the video signal into a plurality of sub-regions;

perform further processing on the plurality of sub-regions including determining that a subset of the plurality of sub-regions corresponds to the sub-section of the display, and determining, in response to determining that the subset of the plurality of sub-regions corresponds to the subsection of the display, that at least one event associated with the medical procedure occurs during the first time period or in proximity to the first time period to confirm that the subset of sub-regions is a region of interest; and automatically identify an object of interest within the selected frame based on the further processing.

18. The system of claim 17, wherein the processor executes the instructions to:

store a file in a database that includes an image corresponding to the selected frame and metadata that labels the identified object of interest on the image; and present the image and the metadata on an output device as a candidate image.

19. The system of claim 18, wherein the processor executes the instructions to:

receive input that confirms the candidate image accurately labels the identified object of interest; and include the candidate image in a data set used to train the neural network to identify the other objects of interest.

20. A method, comprising:

determining, based on eye tracking data, that a clinician gazes at a sub-section of a display for more than a threshold amount of time during a first time period of a medical procedure, the display displaying video of the medical procedure according to a video signal;

identifying a block of the video signal that corresponds to the first time period;

segmenting selected frame in the block of the video signal into a plurality of sub-regions;

performing further processing on the plurality of sub-regions including determining that a subset of the plurality of sub-regions corresponds to the sub-section of the display, and determining, in response to determining that the subset of the plurality of sub-regions corresponds to the sub-section of the display, that at least ono event associated with the medical procedure occurs during the first time period or in proximity to the first time period to confirm that the subset of the plurality of sub-regions is a region of interest; and automatically identifying an object of interest within the selected frame based on the further processing.

* * * * *